United States Patent [19]

Bohl

[11] Patent Number: 4,518,699
[45] Date of Patent: May 21, 1985

[54] ON-LINE COAL ANALYZER

[75] Inventor: Thomas L. Bohl, Madison, Ohio

[73] Assignee: The Babcock & Wilcox Company, New Orleans, La.

[21] Appl. No.: 532,878

[22] Filed: Jan. 30, 1984

Related U.S. Application Data

[62] Division of Ser. No. 395,427, Jul. 6, 1982, abandoned.

[51] Int. Cl.³ .................. G01N 33/22; G01N 35/02
[52] U.S. Cl. .................. 436/49; 73/432 R; 73/863.53; 177/25; 422/63; 422/64; 422/80; 436/43; 436/139
[58] Field of Search .......... 436/43, 47, 48, 49, 436/139, 174, 160; 73/432 Z, 863.53; 422/50, 63, 64, 65, 67, 68, 78, 80; 177/145, 150, 152, 154

[56] References Cited

U.S. PATENT DOCUMENTS

| | | | |
|---|---|---|---|
| 2,597,751 | 5/1952 | Ruge | 177/211 |
| 2,754,178 | 7/1956 | Mack | 436/139 X |
| 3,222,927 | 12/1965 | Messer | 374/36 |
| 3,256,948 | 6/1966 | Annen et al. | 177/211 |
| 3,380,597 | 4/1968 | Czetli | 73/863.53 X |
| 3,499,328 | 3/1970 | Kenny et al. | 73/432 Z |
| 3,643,493 | 2/1972 | Vitovsky | 73/432 Z X |
| 3,684,452 | 8/1972 | Bessman | 422/64 |
| 3,843,323 | 10/1974 | Quame | 436/47 |
| 3,870,465 | 3/1975 | Marechal | 436/68 X |
| 3,909,598 | 9/1975 | Collins et al. | 73/76 X |
| 4,039,287 | 8/1977 | Moran | 422/65 |
| 4,080,168 | 3/1978 | Abu-Samra et al. | 436/175 |
| 4,215,579 | 8/1980 | Hines et al. | 73/863.53 |
| 4,248,315 | 2/1981 | Falinower | 422/64 X |
| 4,401,763 | 8/1983 | Itoh | 436/160 X |
| 4,420,051 | 12/1983 | Furuta et al. | 177/145 X |
| 4,424,062 | 1/1984 | Kamino et al. | 423/461 X |
| 4,437,561 | 3/1984 | Hasegawa et al. | 177/145 X |

FOREIGN PATENT DOCUMENTS 0381766 5/1973 U.S.S.R. .................. 374/36

OTHER PUBLICATIONS

Owings et al., "Methods of Sampling and Analyzing Coal-Mine Dusts for Incombustible Content", Department of Interior Information Circular Jul. 1940.
Nadkaini, Am. Lab. (USA) vol. 13, No. 8, (Aug. 1981), (Class 436/139), pp. 22-29.

Primary Examiner—Arnold Turk
Assistant Examiner—Robert J. Hill, Jr.
Attorney, Agent, or Firm—Vytas R. Matas; Robert J. Edwards

[57] ABSTRACT

A method for on-line analysis of a coal sample. Four radial arms (16) extend from the output shaft (28) of an indexing motor (14). Sample cups (12) at the ends of the arms are indexed along a circular path past a filling station (18) where the cup is filled with pulverized coal, an analyzing station (20) where various chemical analyses are performed on the coal sample, a dumping station (22) where the residue of the coal sample is dumped for disposal, and a cleaning station (24) where the sample cup is cleaned in preparation for another analysis cycle.

4 Claims, 1 Drawing Figure

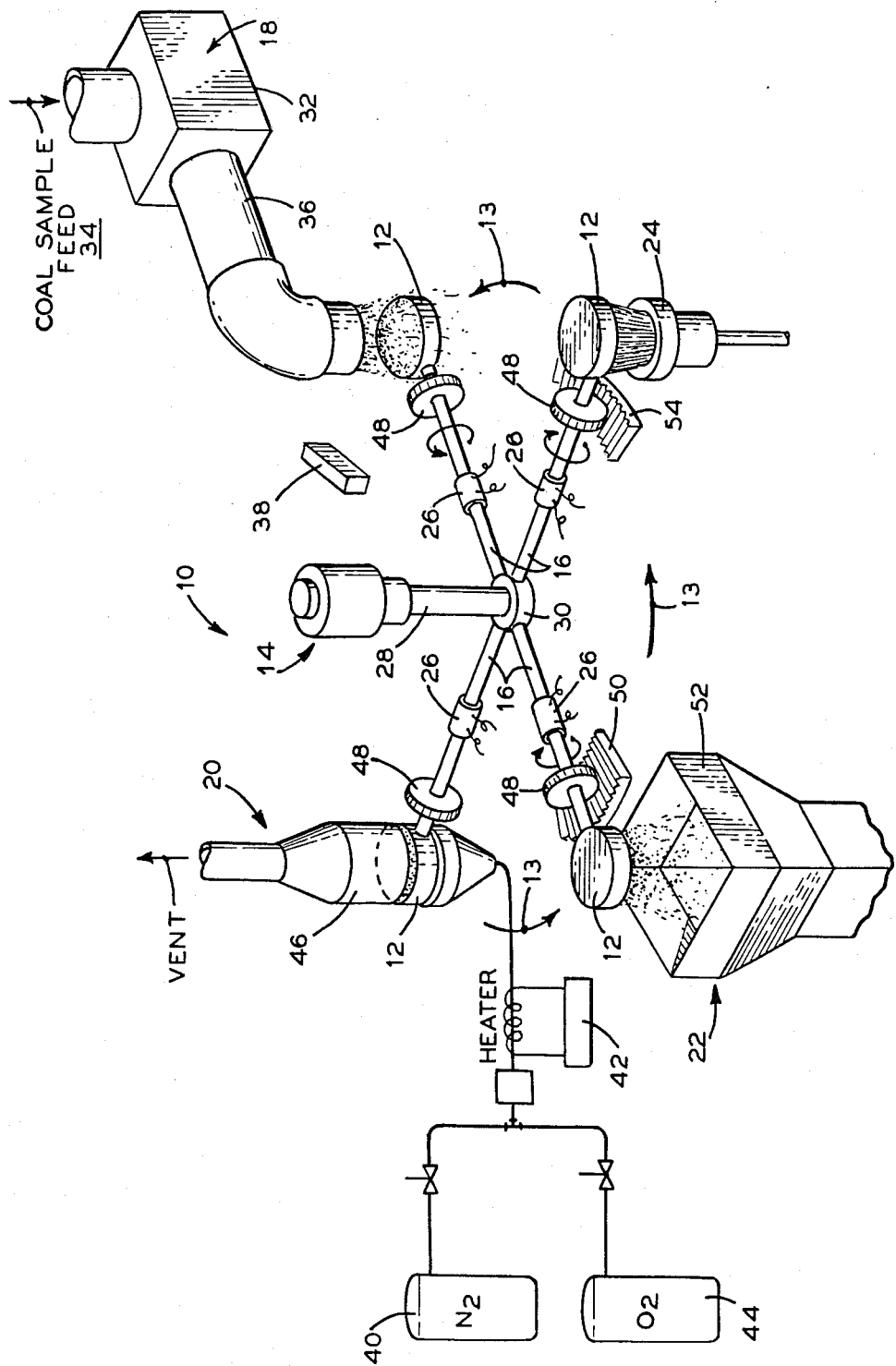

ON-LINE COAL ANALYZER

This is a division, of application Ser. No. 395,427, filed July 6, 1982, now abandoned.

TECHNICAL FIELD

The present invention relates generally to coal analyzers, and more particularly to an on-line coal analyzer wherein chemical analyses are automatically performed on coal samples.

BACKGROUND ART

Coal analysis in the facilities of large coal users is generally accomplished by traditional laboratory techniques performed on coal grab samples. Such sampling requires a plurality of manual manipulations, and the analyses are very time consumming.

Some attempts have recently been made to provide on line, real time analyses. For example, automated instruments have been developed using radiation techniques wherein an instrument straddles a coal feeder belt and irradiates the coal with neutrons or gamma radiation. Re-radiation of the elements of the coal is detected and the coal constituents are determined by computer analysis.

While such devices are effective, they are very large and expensive, and since they deal with inherently dangerous materials they are subject to extensive government licensing and safety procedures which add to the total cost of operation.

Because of the foregoing, it has become desirable to develop an on-line, radiation-free, automatic system for analyzing coal samples.

SUMMARY OF THE INVENTION

The present invention solves the aforementioned problems associated with the prior art as well as other problems by providing a method and apparatus for automatically weighing coal samples and performing chemical analyses of the samples. The apparatus provided can be very compact and relatively inexpensive to construct and maintain. Also no inherently hazardous constituents are used in the analyses.

More specifically, the invention provides a plurality of stations distributed about a central indexing motor drive. A plurality of sampling cups are attached to rotary arms attached to the motor drive. The analyzing system includes a sampling station where coal is automatically extracted from the main coal feed system, an analyzing station where all the chemical analyses are performed, a dumping station where the coal residue is dumped from the sampling cups, and a cleansing station where the sampling cups are cleaned in preparation for the next sampling cycle. There is a sampling cup for each station so that the various steps in the process are performed simultaneously as the sampling cups are indexed to each station. A strain gauge or similar device is provided on each sampling arm so that the weight of each sampling cup can be continuously monitored.

BRIEF DESCRIPTION OF THE DRAWING

The single FIGURE of the drawing is a perspective view schematically representing the apparatus of the invention.

DESCRIPTION OF THE PREFERRED EMBODIMENT

Referring now to the drawing where the illustration is for the purpose of describing the preferred embodiment of the invention and is not intended to limit the invention hereto, the FIGURE illustrates an analyzing system, designated generally by the numeral 10, which comprises a plurality of sampling cups 12, which are indexed along a circular path depicted by the arrows 13 by means of a central indexing motor drive unit 14 which drives the cups through radially extending arms or shafts 16; and a plurality of functional stations including a sampling station 18, an analyzing station 20, a dumping station 22 where the sample residue is dumped into a waste hopper, and a cleaning station 24 where each sample cup is cleaned for reuse in another analyzing cycle.

Each of the sampling cups 12 is a shallow open cylinder made from a porous metal such as sintered stainless steel, inconel, or another durable, inert material. Each of the radial arms 16 has a strain gauge 26 or other suitable device attached to it and connected to a central controller through slip rings or the like to provide accurate monitoring and recording of the weight of each sample cup during the various steps of an analyzing cycle.

In accordance with the preferred embodiment of the invention, the indexing motor drive 14 has a vertical output shaft 28 with a cylindrical head 30 attached to the lower end thereof. As illustrated herein, four radial arms 16 extend horizontally from the head 30, and a sampling cup 12 is fixed to the end of each arm. As will be described in further detail below, the arms 16 are mounted to be rotatable about their longitudinal axes within the head 30.

The sampling station 18 comprises a known type of pulverizer 32 for reducing a coal sample to a particle size suitable for chemical analysis, an inlet feed tube 34 leading from the coal feed system of the facility, and an outlet tube 36 adapted to direct a pulverized coal sample to a waiting cup 12 which has been indexed into position beneath the outlet tube 36. The coal sample can be extracted from the coal feed system continuously by means of an auger or other such known device.

At the sampling station the cup 12 is intentionally overfilled with the excess being returned to the main feed system. Once the cup is filled the indexing unit 14 is energized to rotate the cup 12 toward the analyzing station 20. To insure that a uniform sample is collected a stationary scraper 38 is mounted between the sampling and analyzing stations and is positioned to scrape off the excess sample even with the top of the cup to obtain a known sample volume. Since the volume of the cup is known and the weight of the sample can be determined by means of the strain gauge 26 on the arm 16, the bulk density of the sample can be calculated, for example by means of a microprocessor, in accordance with the equation:

$$\text{bulk density} = \frac{\text{total weight} - \text{tare weight}}{\text{volume}}$$

At the analyzing station 20 the sample is first dried by passing nitrogen or other inert gas from a source 40 through a heater 42, and then through the porous sample cup 12. During the drying operation the weight is monitored and the drying operation is stopped when no further significant weight loss is detected. The moisture content is then calculated by a microprocessor in accordance with the equation:

$$\text{Percent Moisture} = \frac{100 \times (\text{initial sample weight} - \text{final sample weight})}{\text{initial sample weight}}$$

It is understood that during the above drying process the nitrogen temperature is controlled to prevent chemical decomposition of the coal.

After drying, the sample is pyrolized by passing oxygen from a source 44 through the heater 42 and then through the sample.

Analyses of the carbon monoxide, carbon dioxide, sulfur dioxide and nitrogen oxides are also performed at the analyzing station 20. Oxygen content is analyzed and used to control the incoming flow rate. Analyses of carbon monoxide, sulfur and nitrogen oxides can be performed using catalytic sensors placed in a vent hood 46 disposed over the sample at the analyzing station. Oxygen is measured with a known zirconia-based sensor. Electro-chemical carbon dioxide sensors can also be employed.

Other known analytical methods can also be used, for example infrared spectroscopy for carbon monoxide and carbon dioxide, and ultraviolet and visible spectroscopy for sulfur and nitrogen oxides.

Constituent concentrations are totalized during pyrolysis. The process is complete when sample weight has stabilized. Knowing the total volume of oxygen added, a material balance can be run and the total concentration of each constituent in the sample calculated. The remaining sample weight is the ash content of the sample.

Using the temperature rise information and the total volume of oxygen added, a heat balance can be run to yield the calorific content of the coal sample.

After the analyses are completed the indexing motor is energized to rotate the sample cut 12 to the dumping station 22. To permit the cup to be inverted over the dumping station, a gear 48 is mounted on each arm 16, and a rack 50 is located adjacent the station. As the arm approaches the station 22, the gear contacts the rack and rotates 180° when the cup reaches a waste hopper 52 to dump the residue.

The sample cup is then indexed to the cleaning station 24 where mechanical, ultrasonic, and/or chemical means are used to clean the cup until its tare weight returns to within a predetermined range. Adjacent the cleaning station a second rack 54 is located to rotate the cup to its normal, upright position for refilling at the sampling station in preparation for a new analysis cycle.

In the illustrated embodiment all analytical steps are indicated as being performed at a single analyzing station 20, however, it can be appreciated that additional analyzing stations can be provided to analyze other constituents and properties of the coal sample.

Certain modifications and improvements will occur to those skilled in the art upon reading the foregoing. It should be understood that all such modifications and improvements have been deleted herein for the sake of conciseness and readability, but are properly within the scope of the following claims:

I claim:

1. A process for the on-line analysis of coal comprising the steps of rotating a sample cup of known volume around a centrally located drive means, filling said sample cup with a sample of pulverized coal at a first station, weighing said sample, using said weight and volume of said sample to calculate the bulk density of said sample, indexing said sample cup to a second station, performing at least one analysis step on the coal sample at said second station, monitoring the weight of said sample cup during said at least one analysis step to indicate complete drying of said sample when no more weight loss is detected, indexing said sample cup to a third station, dumping the residue of the coal sample at said third station, indexing said sample cup to a fourth station, cleaning said sample cup at said fourth station, and rotating said sample cup back to said first station.

2. The method as defined in claim 1, in which said sample cup is initially overfilled at said first station, and said sample is leveled to the top of said sample cup between said first and second stations to provide a known volume of coal for analysis.

3. The method as defined in claim 1 in which said cleaning step is carried out until the weight of said sample cup is within a predetermined range of the original tare weight of said sample cup.

4. The method as defined in claim 1, 2 or 3, wherein a plurality of said sample cups are indexed simultaneously whereby said filling, analysis, dumping and cleaning steps are performed substantially simultaneously.

* * * * *